United States Patent [19]

Dill et al.

[11] Patent Number: 5,318,686
[45] Date of Patent: Jun. 7, 1994

[54] CAPILLARY ALIGNING DEVICE FOR ON-LINE OPTICAL DETECTION

[75] Inventors: Rand Dill, Corte Madera; Christopher J. Siebert, Berkeley, both of Calif.

[73] Assignee: Bio-Rad Laboratories, Inc., Hercules, Calif.

[21] Appl. No.: 102,438

[22] Filed: Aug. 5, 1993

Related U.S. Application Data

[62] Division of Ser. No. 975,763, Nov. 13, 1992, Pat. No. 5,269,901.

[51] Int. Cl.⁵ .................. G01N 27/26; G01N 27/447
[52] U.S. Cl. .......................... 204/299 R; 204/180.1; 356/344
[58] Field of Search ............ 204/299 R, 180.1; 73/23.4, 61.58, 61.61; 356/344

[56] References Cited

U.S. PATENT DOCUMENTS

| | | | |
|---|---|---|---|
| 4,854,700 | 8/1989 | Cutie et al. | 73/61.52 X |
| 4,898,658 | 2/1990 | Karger et al. | 204/299 R |
| 4,985,129 | 1/1991 | Burd | 204/299 R |
| 5,019,236 | 5/1991 | Young | 204/299 R |
| 5,021,646 | 6/1991 | Weinberger et al. | 204/227.11 |
| 5,085,757 | 2/1992 | Karger et al. | 204/299 R |
| 5,122,253 | 6/1992 | Christianson | 204/299 R |
| 5,124,020 | 6/1992 | Wang | 204/299 R |
| 5,164,064 | 11/1992 | Dill et al. | 204/299 R |
| 5,169,511 | 12/1992 | Allington et al. | 204/299 R |
| 5,198,091 | 3/1993 | Burolla et al. | 204/299 R |
| 5,208,466 | 5/1993 | Pentoney, Jr. | 204/299 R X |
| 5,235,409 | 8/1993 | Burgi et al. | 356/436 |
| 5,239,360 | 8/1993 | Moring et al. | 356/344 |
| 5,274,227 | 12/1993 | Moring | 356/344 X |

Primary Examiner—John Niebling
Assistant Examiner—John S. Starsiak, Jr.
Attorney, Agent, or Firm—Townsend and Townsend Khourie and Crew

[57] ABSTRACT

A cartridge for high performance capillary electrophoresis is constructed to accommodate a capillary with a flexible length of tubing surrounding it for the passage of a liquid coolant. Connections and fittings in the cartridge permit quick insertion and removal of the capillary and coolant tube so that capillaries of different lengths can be used with the same cartridge. Apertures in the cartridge body permit the capillary and tubing to be looped outside the cartridge so that different lengths can be connected without the need to coil the capillary inside the cartridge body. A removable capillary aligning device is also disclosed, which fits in the cartridge in a fixed orientation and holds the capillary in alignment with lenses if used and a light beam passing through the cartridge.

4 Claims, 4 Drawing Sheets

CAPILLARY ALIGNING DEVICE FOR ON-LINE OPTICAL DETECTION

This is a division of application Ser. No. 07/975,763 filed Nov. 13, 1992 now U.S. Pat. No. 5,269,901.

This invention relates to capillary electrophoresis, and in particular to cartridges which contain liquid-cooled capillary tubes and which are designed for use in automated electrophoresis equipment.

BACKGROUND OF THE INVENTION

Capillary electrophoresis has proved to be a highly effective means of analyzing extremely small biological samples. The long separation path in a capillary permits the separation of a multitude of components in a single sample, including components which are closely related. In addition, the thin diameter of a capillary permits the use of high voltages, which produce separations in a relatively short period of time. Furthermore, capillaries are particularly well suited for on-line detection of the separated species by passing a light beam through the capillary itself directly into a detector.

The unusually high resolution obtained in capillary electrophoresis is attributable to the small internal radius of the capillary which facilitates the efficient removal of the joule heat generated by the high-voltage electric current. As the separations attempted in capillaries become increasingly sensitive, the need for efficient heat transfer from the capillary becomes more significant. In coolant systems in general, liquid cooling is far more efficient than air cooling, and it is reasonable to expect that this would apply to capillaries as well.

Capillary cartridges designed for circulating liquid coolant have indeed been developed, but they suffer from a number of disadvantages. Due to the geometries involved, it is far more difficult to devise a liquid-cooled capillary cartridge than an air-cooled cartridge. The reasons include the fact that the ends of the capillary must be electrically isolated so that electrical potential differences of up to 30,000 V can be applied. Furthermore, the tips of the capillaries must extend into reservoirs containing buffer solutions which serve as liquid junctions to communicate the capillary tips with electrodes. Still further, to be adaptable for use with a variety of sample mixtures of different compositions, the capillary must be exchangeable with capillaries of different lengths and diameters. Capillary lengths in common use, for example, range from 20 cm to 100 cm.

In its most widely used configurations, the capillary is arranged with its tips directed vertically downward and terminating at the same elevation, for purposes of hydrostasis. The capillary in these configurations thus forms an arch terminating at the downward-directed tips. In water-cooled systems presently known, the capillary is coiled within a cartridge housing of relatively compact volume through which the liquid coolant circulates. Coiling permits a single cartridge housing to accommodate different capillary lengths, while facilitating efficient cooling and reducing the overall dimensions of the cartridge. This however limits the selection of different capillary lengths to multiples of the coiling circumference, and the circumference itself is generally dictated by the size and structure of the cartridge. Furthermore, the coiling prevents the achievement of uniform heat transfer, despite the construction of coolant flow conduits in the capillary which are shaped to direct and confine the coolant to the vicinity of the capillary coils.

A further problem with the coiling of capillaries is what might be termed the "race-track" effect, i.e., the difference in path length along the capillary as a function of cross-sectional position, ranging from a relatively short path closest to the center of the coil to a relatively long path furthest from the center. The degree of difference and hence the severity of the effect are proportional to the number of turns in the coil. This can be significant, since coils of several turns are commonly used to achieve optimal resolution and separation of the solute peaks. Recent studies have confirmed that coiled capillaries suffer a loss of resolution relative to straight capillaries run under otherwise identical conditions. As more sensitive separations are attempted and performance expectations increase, the race-track effect will take on greater significance and its avoidance will become more important.

The need to immerse the capillary tips in the buffer reservoirs raises a further consideration in liquid-cooled systems. To permit the immersion, the tips protrude from the cooled volume through ports which are sealed around the outer diameter of the capillary with wax or glue. Any areas which are left uncooled introduce errors and variations in the detection results. Since the protruding tips are uncooled, cartridges of this type must be designed so that the ratio of the combined lengths of the protruding tips to the total capillary length is as small as possible.

Another major consideration in capillary electrophoresis is the accurate alignment of an optical detection system with the capillary wall for on-line detection. At least one window along the capillary must be provided for optical detection, and it must be properly aligned with the lenses in the cartridge housing which form the light path through the cartridge. In systems designed for capillary exchangeability, the ease of alignment is even more critical since proper alignment must be achieved each time the capillary is changed. In liquid-cooled cartridges currently known, the segment of the capillary which is designated as the window is aligned in a precise manner with a fixed external window in the cartridge envelope or housing, then sealed with wax or adhesive to isolate the external surface of the segment from the coolant. Accurate alignment assures reproducible results but requires significant time and detailed effort.

What does not presently exist, and is strongly needed, is the means to rapidly and conveniently exchange capillaries in a cartridge while maintaining efficient cooling without coiling or tedious optical alignment procedures. A system which can meet these requirements will significantly help capillary electrophoresis to achieve its full potential.

SUMMARY OF THE INVENTION

The present invention provides a cartridge which accommodates a capillary surrounded by a length of flexible tubing which permits the circulation of a liquid coolant over the capillary. Apertures in the cartridge wall permit the tubing-surrounded capillary to be looped outside the cartridge, so that capillaries of any length may be mounted to the cartridge and cooled along their entire length without coiling. Coolant connections and fittings inside the cartridge permit the capillary and tubing to be readily removed and replaced with capillary and tubing of different lengths, each time easily restoring a seal around the coolant channels.

This invention further provides an insert for the cartridge which receives a portion of the capillary which is exposed beyond one end of the flexible tubing and secures it in proper alignment with lenses if used and a light beam for detection purposes. The insert optionally includes recesses to hold lenses, a slot into which the capillary is inserted laterally, a guide wall at the end of the slot which places the capillary in alignment with the lenses, and a keeper to hold the capillary in place against the guide wall.

Further features, advantages and embodiments of the invention will become apparent from the description which follows.

DETAILED DESCRIPTION OF THE INVENTION AND PREFERRED EMBODIMENTS

Figure 1:
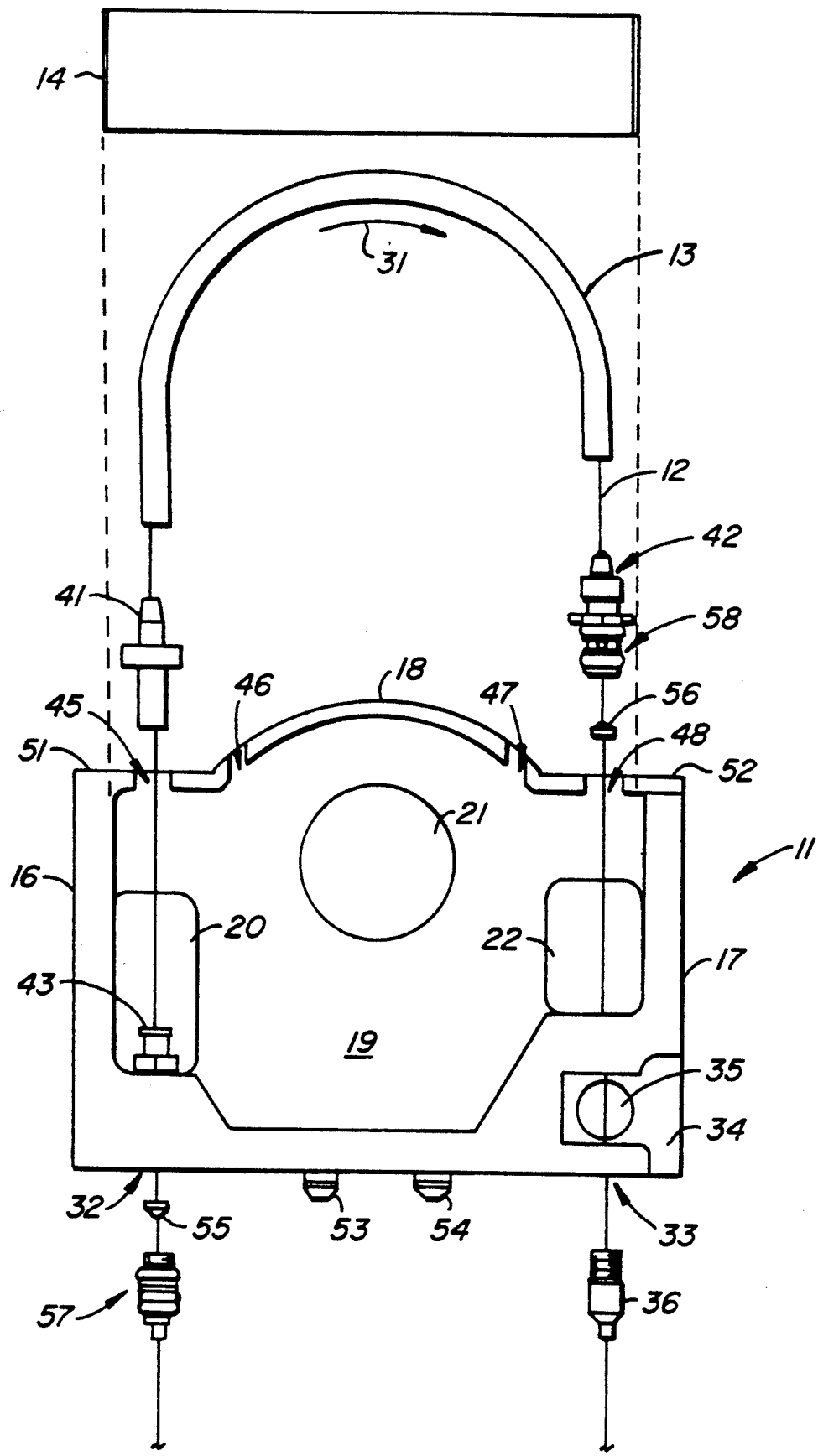
FIG. 1 is an exploded front elevation view of a capillary cartridge representing one illustrative embodiment of the present invention.

An exploded view of an illustrative cartridge embodying features of the present invention is shown in FIG. 1. The components shown include the cartridge body 11, which serves as a frame or housing for the other parts, the capillary 12, the coolant tube 13, a cover 14 for the cartridge body, and various seals and connective fittings.

The cartridge body 11 is a flat unitary structure with raised edges along the bottom 15, sides 16, 17 and top 18. The top edge 18 is raised slightly less than the edges along the bottom and sides. This permits the cartridge cover 14 to be slid downward past the top edge, inserted into grooves (not visible in the drawing) along the inner surfaces of the side edges 16, 17, and slid along the grooves down over the recessed center 19 of the cartridge. Thus inserted, the cartridge cover 14 protects the capillary 12 and coolant tube 13 from inadvertent contact with external objects or other instrument parts and holds them in place. The cartridge body contains three openings 20, 21, 22 to lighten its mass and to improve visibility and the ease of threading the capillary 12 through the cartridge ports.

The fully assembled cartridge when inserted in the instrument connects to the instrument components in such a manner that electrophoretic migration of solutes through the capillary proceeds in the direction indicated by the arrow 31. The upstream point at which the capillary enters the cartridge body, according to this direction of solute migration, is thus the inlet port 32, and the downstream point at which the capillary leaves the cartridge body is the outlet port 33. Immediately upstream of the outlet port 33 is a rectangular recess 34 in the cartridge body, and in the center of the recess is a circular opening 35. The recess and opening are designed to receive a capillary aligning device through which the capillary passes as well as the detection beam. As described in detail below, the capillary aligning device is designed for easy assembly and insertion while assuring proper alignment of the capillary detection window with the lenses and the detection beam. A threaded fitting 36 with a hole for passage of the capillary is screwed into the bottom edge of the recess to secure the capillary aligning device in place.

The capillary 12 and coolant tube 13 are shown extended in FIG. 1 to illustrate how the fittings are arranged. In use, however, the coolant tube 13 extends into the interior of the cartridge body, and is tightly secured at both ends over tube fittings 41, 42 by a resistance fit, the tube fittings in turn fitting into ports 43, 44 in the cartridge body. The connections are fluid-tight connections, which in this particular embodiment are achieved by matched tapers on the inlet fitting 41 and port 43, and O-ring seals between the outlet fitting 42 and port 44. The coolant tube 13 thus covers the full length of the capillary 12 extending between the two ports 43, 44.

In the embodiment shown in the drawing, the ports are integrated into the structure of the cartridge body 11. As an alternative, the ports may be in separate structures or inserts designed to be removable from or movable on the cartridge body, so that they can be exchanged or the connections modified.

Returning to the drawing, the top edge 18 of the cartridge body has four openings 45, 46, 47, 48. One of these 45 is aligned with the inlet-side ports 32, 43 of the cartridge body, and another 48 is aligned with the outlet-side ports 33, 44. These openings facilitate the threading of the capillary ends through these ports, permitting the user to avoid having to bend the capillary tightly or to put pressure on a bent section while making the insertions. The openings 20, 22 in the cartridge body further help guide the insertion by permitting the user to grasp the capillary from front and back at a location close to the point of insertion.

Once the capillary ends are inserted, the capillary is pushed through far enough so that the coolant tube fittings are joined to those in the cartridge body. During this process or after it, depending on the length of the capillary, the capillary and coolant tube are then lifted forward out of the two openings 45, 48 which are aligned with the capillary ports. This renders the surfaces 51, 52 accessible for clamping the cartridge into the instrument. If the capillary and coolant tube are short enough that they can fit inside the cartridge body without coiling, they are then placed under the curved portion of the raised top edge between the two inner openings 46, 47. If the length of the capillary and coolant tube is too great to fit in this space, they can be passed through the two inner openings 46, 47 so that the loop is outside the cartridge body. With this arrangement, the cartridge can accommodate a capillary of any length without coiling.

Coolant liquid is supplied to the cartridge body by coolant ports 53, 54, and internal channels in the cartridge body connect these ports with the coolant tube 13. Leakage of the coolant liquid from these channels is prevented by gasket seals 55, 56, and retaining fittings 57, 58. The channels and the placement of these seals and fittings are shown in FIGS. 2 and 3.

Figure 2:
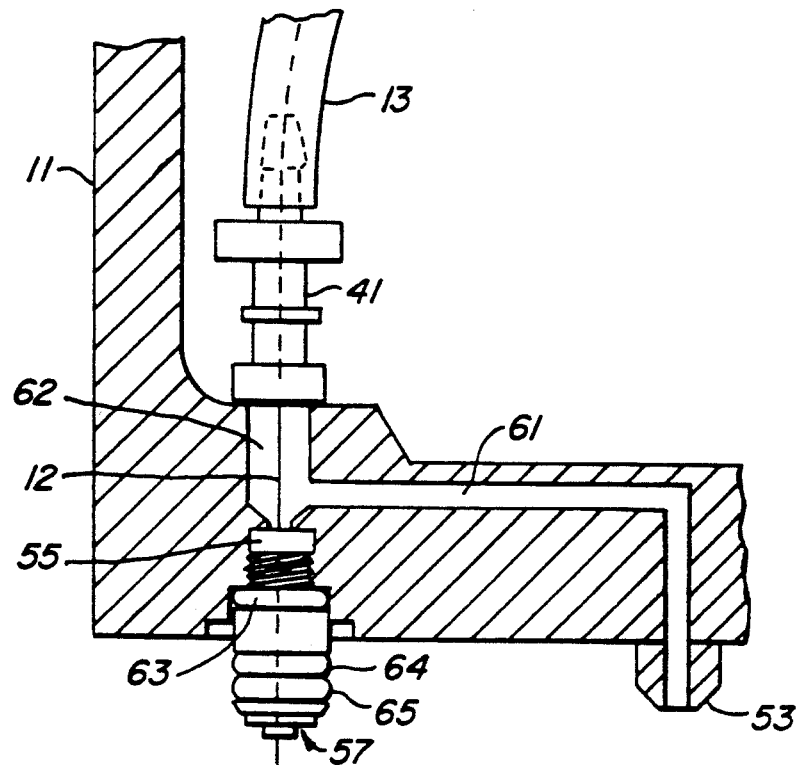
FIG. 2 is a detailed view in partial cross section of one corner of the cartridge shown in FIG. 1.

A detailed view of the inlet side of the cartridge body is shown in FIG. 2. In this view, the cartridge body 11 is shown in cross section while the remaining components are not. Coolant flows from the coolant inlet port 53 through an internal channel 61 to a chamber 62 where it surrounds the segment of the capillary 12 which extends beyond the end of the coolant tube 13. The coolant enters the coolant tube 13 through the tube fitting 41 and passes up into the arch of the tube. At the base of the chamber 62 is the gasket seal 55 which is seated against an inverted shoulder beneath the chamber and which contains a small central passage for the capillary. The gasket seal 55 is compressed around the capillary by the threaded retaining fitting 57, sealing the chamber against outward leakage of coolant, the contacting faces of the gasket seal and the fitting being tapered in a complementary manner to force the seal inward against the capillary. Further leak prevention is provided by an internal O-ring 63, while external O-rings 64, 65 remain exposed to seal against the inside of a port in the instrument.

Figure 3:
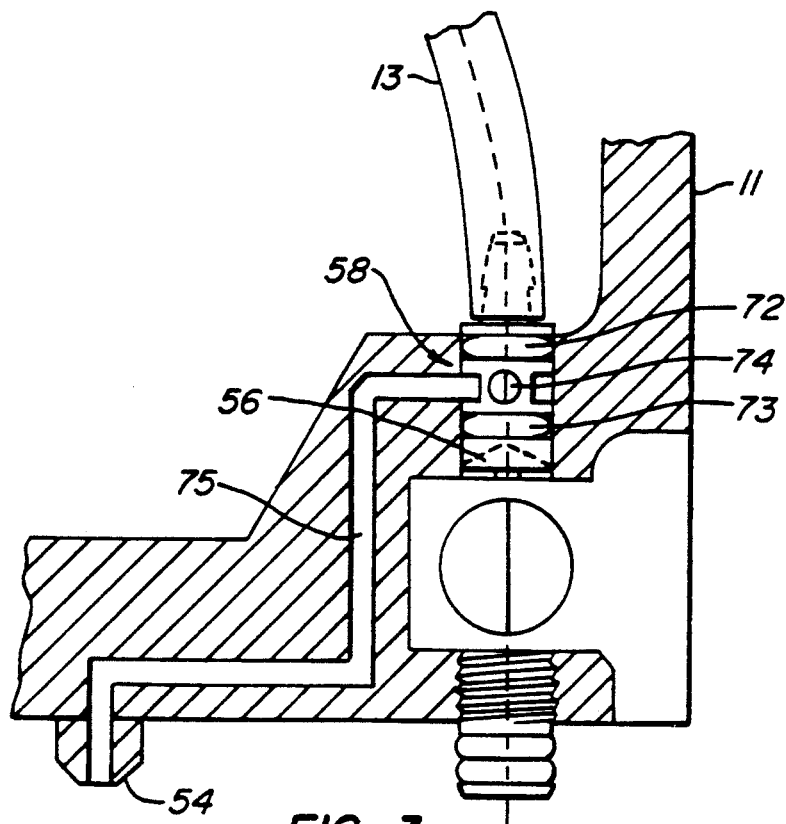
FIG. 3 is a detailed view in partial cross section of another corner of the cartridge shown in FIG. 1.

FIG. 3 is a detailed view of the outlet side of the cartridge body. Here as well the cartridge body 11 is shown in cross section. Coolant flows from the coolant tube into the interior of the retaining fitting 58 which is hollow and positioned inside a chamber 71 inside the cartridge body. The coolant is prevented from leakage around the periphery of the fitting 58 by O-rings 72, 73 at the top and bottom of the chamber, respectively, and is also prevented from leakage around the capillary by a second gasket seal 56 similar to that used to seal the inlet chamber 62, although inverted. As in the inlet side, the contacting faces of the gasket seal 56 and the fitting 58 are tapered to compress the gasket around the capillary. An opening 74 in the fitting communicates the hollow interior of the fitting with the chamber 71, thereby permitting the coolant to pass into the chamber. From the chamber, the coolant passes into an internal coolant channel 75, and from there to the exit port 54.

Figure 4A:
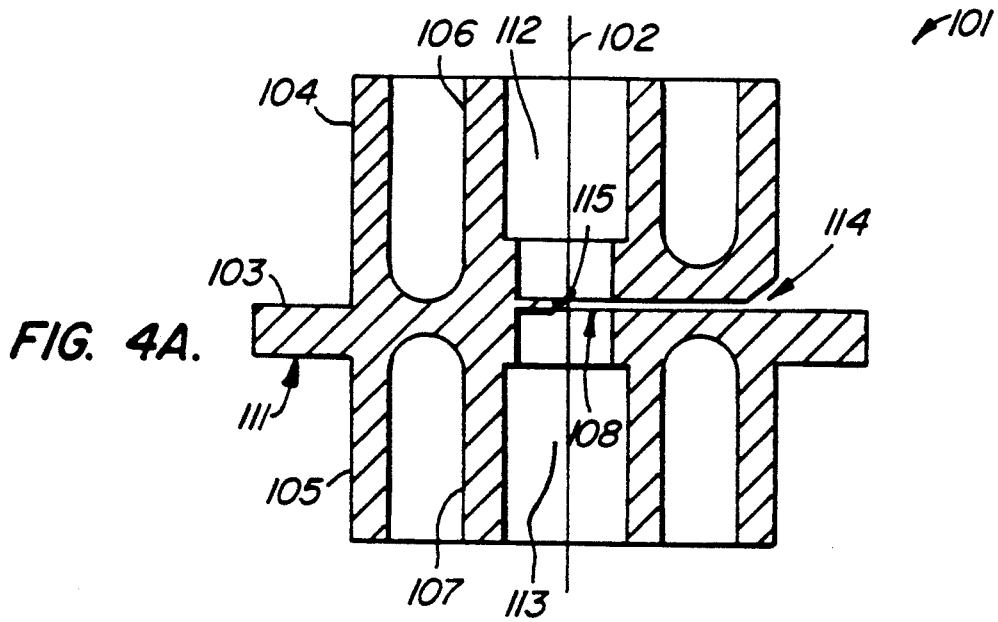
FIG. 4A is a cross section view of one illustrative embodiment of a lens holder of the present invention.
Figure 4B:
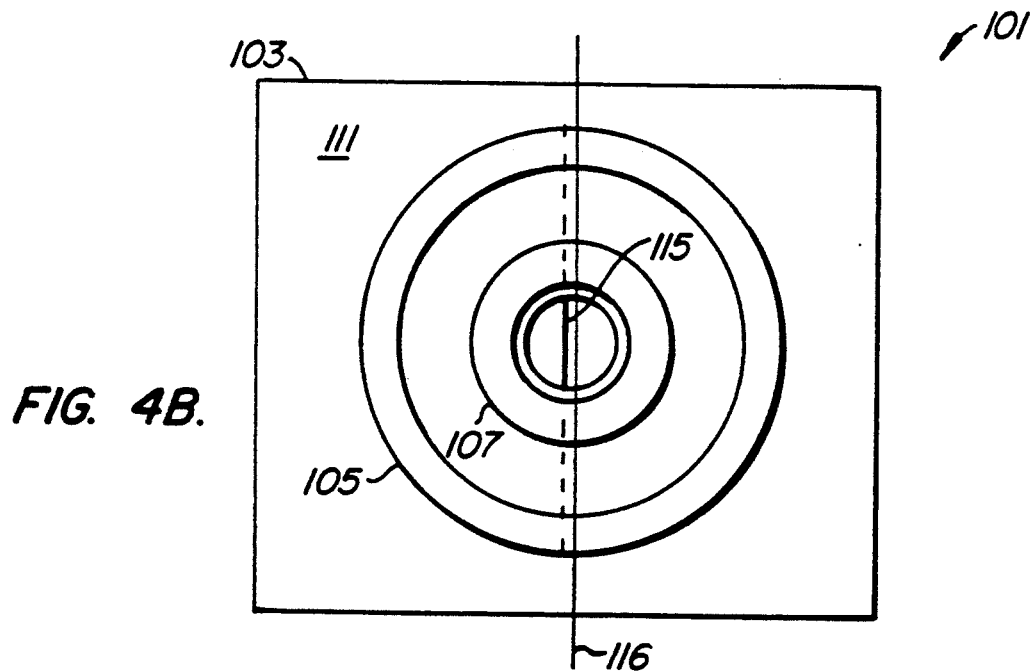
FIG. 4B is a plan view of the capillary aligning device of FIG. 4A, the view rotated 90° from that of FIG. 4A.

FIGS. 4A and 4B depict the capillary aligning device 101. This is a removable portion of the cartridge which holds a pair of lenses, receives the capillary between the lenses and provides openings for the detector light beam to pass through the lenses and the capillary. When the capillary aligning device is placed in the cartridge and the cartridge is inserted in the instrument, the capillary aligning device places the two lenses and the short segment of the capillary which passes between them in the light path of the detector. The direction of the light path is indicated by the line 102 in FIG. 4A.

The capillary aligning device is shaped from a rectangular plate 103 with a pair of raised cylindrical rims 104, 105 extending from either side of the plate. Inside these cylindrical rims are a second pair of cylindrical rims 106, 107, coaxial with the first. These inner cylindrical rims 106, 107 are connected by an opening 108 for passage of the detector beam. The common axis of all four cylindrical rims is the light path itself 102. The rectangular plate is sized to fit within the similarly sized rectangular recess 34 in the cartridge body (FIG. 1) to assure proper placement of the capillary aligning device in the cartridge. When the lens holder is placed in the cartridge, one surface 111 of the rectangular plate contacts the rear surface of the recess, and one of the outer cylindrical rims 105 of the capillary aligning device protrudes passes through the circular opening 35 (FIG. 1) in the rear surface of the recess, further assuring proper alignment.

The lenses (not shown) are placed in the recesses 112, 113 formed by the inner cylindrical rims 106, 107. Ball lenses are a preferred type of lens, and the inner cylindrical rims are sized to receive the ball lenses in a snug fit. The outer cylindrical rims 104, 105 provide protection for the lenses in addition to that afforded by the inner cylindrical rims. The outer cylindrical rims are also long enough to extend outward beyond the two flat faces of the cartridge body when the capillary aligning device is inserted, thereby protruding from both sides of the cartridge. This makes the rims accessible for contact by cradle members of complementary curvature in the instrument (not shown in the Figures). The cradle members are aligned with the components of the optical detection system, and the engagement of the outer cylindrical rims with the cradle members thereby provides a means of obtaining and securing the proper alignment of the capillary and lenses with these components.

Figure 4C:
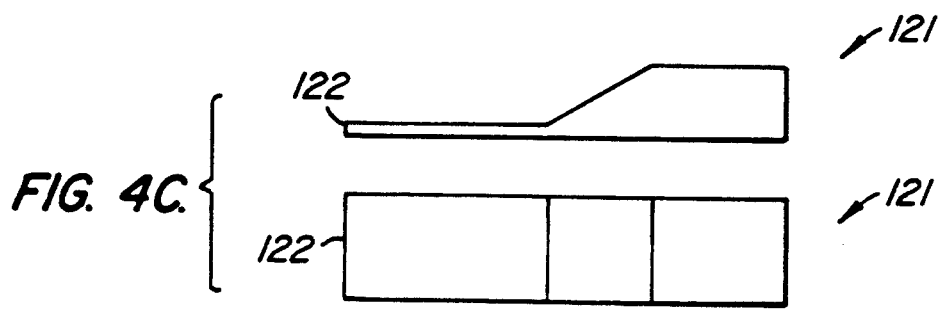
FIG. 4C includes two views of an insert for the capillary aligning device of FIGS. 4A and 4B.

Insertion of the capillary into the capillary aligning device is done through a slot 114 which is cut parallel to the rectangular plate 103 halfway across the inner and outer cylindrical rims 104, 106 on one side. The inner terminus of the slot is a straight wall 115 which is parallel to and slightly displaced from the center line 116 of the capillary aligning device. The displacement is arranged such that when the capillary is held against the straight wall 115, the central axis of the capillary crosses the central axis of the light path 102. Once the capillary is inserted, a capillary keeper 121 (FIG. 4C) is inserted into the slot. The fit of the capillary keeper is tight enough to hold it in place by friction yet loose enough for easy manual insertion and removal, and the keeper has a straight forward edge 122 which contacts the capillary and holds it against the straight wall 115 inside the slot. Accordingly, the combination of the straight end wall 115 of the slot, the capillary keeper 121, and the mating of the outer cylindrical rims 104, 105 with the cradle members in the instrument together afford a quick, easy and accurate alignment of the capillary, lenses and optical path.

While the slot 114 in the embodiment shown in these drawings is perpendicular to the light path 102, the slot may alternatively be at an acute angle with the light path such that the capillary itself when secured into position in the slot will also be at an acute angle to the light path. This offers advantages in certain types of detection systems. In general, the slot will be transverse to the light path, i.e., crossing it at either a 90° angle or some other angle.

Figure 5:
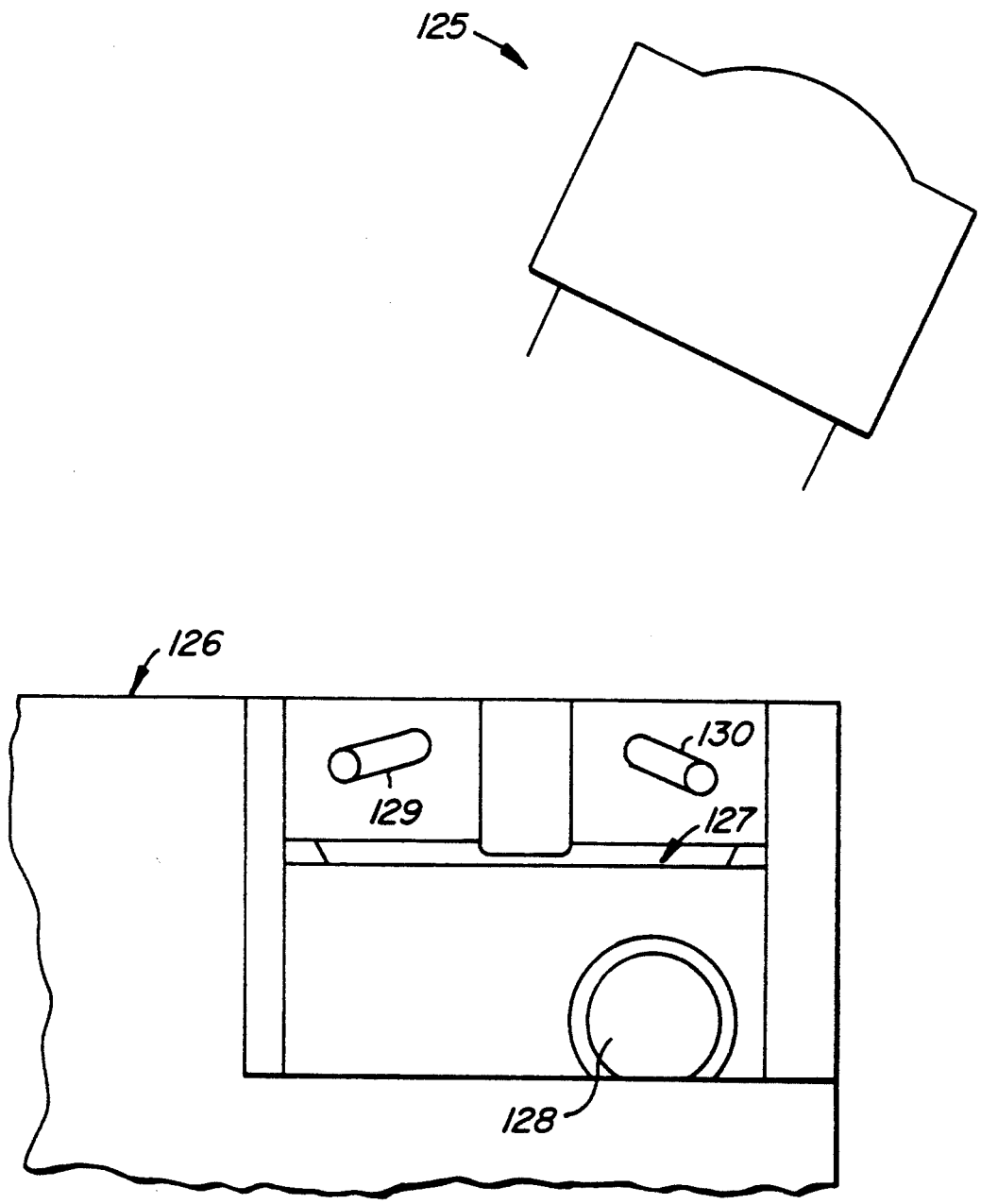
FIG. 5 is a front elevation of the capillary cartridge of the preceding figures, shown together with an instrument providing fluid and electrical connections as well as a detection unit for use with the cartridge.

Turning finally to FIG. 5, the capillary cartridge 125 is shown poised for placement inside the instrument 126 which houses components and connections for loading sample into the capillary, supplying a voltage to the capillary through electrode buffers, supplying coolant to the coolant inlet port and circulating the coolant through the coolant channels and coolant tube to leave through the coolant exit port, as well as a light source and detector for analyzing the separated solutes, and controls and programming for automated operation. Typically, the instrument will be computer controlled, and will be designed to analyze a multitude of samples in succession, and to identify the separated components of the sample and print out their identification and quantity.

The cartridge is held in the retracted position as shown, and installed into the instrument by insertion in a slot 127.

Once the cartridge is in place in the instrument, and all fluid connections are made and the light path of the cartridge is in alignment with the light source 128 of the instrument and the detector (not shown), the cartridge may be secured in place by a pair of rotatably mounted handles 129, 130. These handles engage the clamping surfaces 51, 52 at the top of the cartridge body (FIG. 1). To remove the cartridge after use, the handles 129, 130 are rotated upward and outward to clear the cartridge, and the cartridge is easily removed. A recess 131 along a rear wall of the instrument above the slot provides finger access to the cartridge for easy removal.

The components of the invention may be fabricated from conventional materials of construction. The primary consideration is that the materials be electrically insulating. Otherwise, the materials are not critical and can be varied widely.

The foregoing is offered primarily for purposes of illustration. It will be readily apparent to those skilled in the art that modifications of the features shown and described herein, as well as variations thereon and substitutions therefor can be made without departing from the spirit and scope of the invention.

What is claimed is:

1. A capillary aligning device capable of being inserted in a capillary cartridge for aligning a capillary of a selected outer diameter in an optical detector path for on-line optical detection in capillary electrophoresis, said device comprising:

first and second hollow cylindrical members joined end-to-end along a common axis to form a junction containing a port to permit passage of a detector beam along said axis;

a slot in said junction transverse to said axis and of sufficient width to receive said capillary, said slot extending across said axis and terminating in an end wall parallel to said axis and displaced therefrom by a distance approximately half the length of said outer diameter of said capillary; and an insert sized to be received within said slot, and when so received to stabilize said capillary against said end wall.

2. A capillary aligning device in accordance with claim 1 in which said junction is extended in directions transverse to said axis to form a flat plate.

3. A capillary aligning device in accordance with claim 1 in which said first and second hollow cylindrical members are defined as a first pair of hollow cylindrical members, said device further comprising a second pair of hollow cylindrical members coaxial with and encircling said first pair.

4. A capillary aligning device in accordance with claim 1 in which at least one of said hollow members is sized to receive a lens.

* * * * *